United States Patent [19]

Kangas et al.

[11] Patent Number: 5,775,330
[45] Date of Patent: Jul. 7, 1998

[54] NEUROMETRIC ASSESSMENT OF INTRAOPERATIVE ANESTHETIC

[75] Inventors: Lars J. Kangas, West Richland; Paul E. Keller, Richland., both of Wash.

[73] Assignee: Battelle Memorial Institute, Richland, Wash.

[21] Appl. No.: 681,196

[22] Filed: Jul. 22, 1996

[51] Int. Cl.$^6$ ........................................... A61B 5/04
[52] U.S. Cl. ................................ 128/731; 128/923
[58] Field of Search ........................... 128/731–733, 128/923; 395/22–24

[56] References Cited

U.S. PATENT DOCUMENTS 5,601,090  2/1997  Musha ........................ 128/732

OTHER PUBLICATIONS

Edmonds, H., "Anesthetic adequacy, surface EMG and quantitated EEG," Acta Anaesthesiol Scand 1993:37(S100): 102–104, 1993.
Gurman, G., "Assessment of depth of general anesthesia," International Journal of Clinical Monitoring and Computing, Kluwer Academic Publishers, 11:185–189, 1994.
Muthuswamy, J., Roy, R., "Bispectrum analysis of EEG of a dog to determine the depth under halothane anesthesia," (IEEE), pp. 5–6, 1993.
Sharma, A., Roy, R., "Design of a recognition system to monitor the depth of anesthesia," Becton Dickinson and Company.

Yli-Hankala, A., Edmonds, H., Heine, M., Strickland, T., Tseuda, K., "Auditory steady state response, upper facial EMG, EEG and heart rate as predictors of movement after isoflurane–nitrous oxide anesthesia," in press, British Journal of Anesthesia.

Primary Examiner—Francis Jaworski
Attorney, Agent, or Firm—Paul W. Zimmerman

[57] ABSTRACT

The present invention is a method and apparatus for collecting EEG data, reducing the EEG data into coefficients, and correlating those coefficients with a depth of unconsciousness or anesthetic depth, and which obtains a bounded first derivative of anesthetic depth to indicate trends. The present invention provides a developed artificial neural network based method capable of continuously analyzing EEG data to discriminate between awake and anesthetized states in an individual and continuously monitoring anesthetic depth trends in real-time. The present invention enables an anesthesiologist to respond immediately to changes in anesthetic depth of the patient during surgery and to administer the correct amount of anesthetic.

20 Claims, 4 Drawing Sheets

NEUROMETRIC ASSESSMENT OF INTRAOPERATIVE ANESTHETIC

This invention was made with Government support under Contract DE-AC06 76RL0 1830 awarded by the U.S. Department of Energy. The Government has certain rights in the invention.

FIELD OF THE INVENTION

The present invention relates generally to a method and apparatus for neurometric assessment of intraoperative anesthetic. More specifically, the present invention is the use of brain wave data processed by a trained neural network to continuously ascertain the level of consciousness of an individual and a consciousness trend before during and after exposure to anesthetic.

BACKGROUND OF THE INVENTION

During administration of anesthesia to a patient, it is important to monitor the patient's awareness or consciousness. Measurements of autonomic indicators such as heart rate, blood pressure, pulse amplitude, sweating, tearing, or mydriasis are commonly used during anesthesia for assessing awareness. In addition, anesthetic is typically administered in fixed amounts based upon weight of a patient. Despite the wealth of studies documenting their unreliability, these anesthetic administration methods prevail today.

There is evidence that the brain is aware of sensory information during conventionally deep anesthesia. Cases of undetected awareness with postoperative recall have resulted in devastating psychiatric complications. Patients in intraoperative cases have described their experiences as the most terrifying imaginable. A few cases involved intense pains, although most fears during intraoperative awareness are caused by overwhelming feelings of helplessness due to the inability to move or communicate. Accordingly, there is a need for improved anesthetic administration and monitoring of patient awareness.

Work has been done quantifying EEG data and anesthetic adequacy by Edmonds, H., "Anesthetic adequacy, surface EMG and quantitated EEG," Acta Anaesthesiol Scand 1993:37 (S100):102–104, 1993. In this paper, EEG data are shown to be of limited value when analyzed by zero crossing analysis because it may only be helpful if there is an abnormally low delivery of anesthetic. Edmonds suggests that EMG (facial muscles) and auditory invoked potentials may be needed to supplement the EEG data for anesthetic monitoring. Thus, this work is of limited value toward real time monitoring of anesthetic depth because it requires three methods and is sensitive to patient variability.

Research reported by Gurman, G., "Assessment of depth of general anesthesia," International Journal of Clinical Monitoring and Computing, Kluwer Academic Publishers, 11:185–189, 1994, discusses a number of techniques for monitoring depth of anesthesia. However, Gurman points out that no single technique is sufficiently reliable to be adequate. He therefore proposes a combined technique using spectral edge frequency of EEG data together with blood pressure monitoring to monitor anesthetic depth.

Additional work by Muthuswamy, J., Roy, R., "Bispectrum analysis of EEG of a dog to determine the depth under halothane anesthesia," (IEEE), pp 5–6, 1993, demonstrates the use of EEG data reduced by fast Fourier transform to determine anesthetic depth. However, Muthuswamy states that power spectra suppresses phase relations and therefore uses a bispectrum analysis. However, the bispectrum analysis was reliable in 14 out of 18 cases when the dog was asleep and 10 out of 15 cases when the dog was awake. Hence, this method is not useful as a real-time anesthetic depth monitor because it is not sufficiently reliable.

Sharma, A., Roy, R., "Design of a recognition system to monitor the depth of anesthesia," Becton Dickinson and Company, show a recognition system that combines EEG auto-regression data in a feedforward neural network with hemodynamic parameters to achieve a recognition rate up to 94%. The EEG auto-regression data in a feedforward neural network alone had a recognition rate of 85% and the hemodynamic parameters alone had a recognition rate of 65%. However, Sharma and Roy bin their output data into three categories, 1.0 for totally asleep, 0.5 for partially asleep, and 0.0 for awake. Accordingly, Sharma and Roy are only able to detect changes between the three categories. Changes in anesthetic depth within a single category are undetectable.

Yli-Hankala, A., Edmonds, H., Heine, M., Strickland, T., Tseuda, K., "Auditory steady state response, upper facial EMG, EEG and heart rate as predictors of movement after isoflurane-nitrous oxide anesthesia," in press, British Journal of Anesthesia, compares various existing measures of depth of anesthesia. The authors do not propose any new methods.

Medical diagnosis and in particular diagnosis based on spectral analysis is limited by the ability of a physician or medical team to assimilate all of the relevant data including relationships between multiple spectral channels.

An artificial neural network (ANN) is an algorithmic system implemented in either software or hardware. An ANN-based model is potentially a superior model because almost all of its free variables are adjustable to behave as a specific instance of a system and because less a-priori knowledge is needed.

An ANN is a network of neurons or processing elements (PE) and weighted connections. The connections correspond to axons and the weights to synapses in the biological brain. A PE performs two functions. It sums the inputs from several incoming connections and then applies a transfer function to the sum. The resulting value is propagated through outgoing connections to other PEs. Typically, these PEs are arranged in layers; with the input layer receiving inputs from the real-world and each succeeding layer receiving weighted outputs from the preceding layer as its input. Hence the creation of a feed forward ANN in which each input is fed forward to its succeeding layer. The first and last layers in this ANN configuration are typically referred to as input and output layers. (Input-layer PEs are not true PEs in that they do not perform a computation on the input.) Any layers between the input and output layers (usually 0–2 in number) are called hidden layers because they do not have contact with any real-world input or output data.

In addition to simple feedforward ANNs, some feedforward ANNs are recurrent ANNs. These networks have feedback connections that move intermediately processed data or output data back to previous layers. These feedback connections allow the ANNs to capture temporal information in data and, thus, model dynamic systems.

Back propagation is one of several possible learning rules to adjust the connection weights during supervised learning (learning by example). Learning occurs when the network weights are adjusted as a function of the error found in the output of the network. The error is the difference between the expected output and the actual output. The weights are adjusted backwards (back-propagated) through the ANN network until the error is minimized for a set of training data.

ANNs have been applied to an increasing number of real-world problems of considerable complexity. Their most important advantage is in solving problems that are too complex for conventional technologies; that is, problems that do not have an algorithmic solution or for which an algorithmic solution is too complex to be found.

In the medical field, ANN has been used to aid in imaging, for example, imaging of pap smears for identification of malignant cells. These systems have been developed to catalog or classify a cell as to whether or not the cell is malignant. In these systems, cell classification is independent from the characteristics of an individual and is simply visual characteristics of the cell in question. A classification system, in general, lacks the capability to identify time related trends.

However, in spite of the advances in artificial neural networks and their specific application to certain medical problems, until the advent of the present invention, there remained a need for an improved method of monitoring anesthesia.

SUMMARY OF THE INVENTION

It is an object of the present invention to provide a developed artificial neural network based method capable of analyzing EEG data to discriminate between awake and anesthetized states in an individual.

It is a further object of the present invention to concurrently determine whether an individual is deeper or shallower in anesthesia in reference to another point in time.

The present invention cannot determine whether the patient is adequately anesthetized. Adequate anesthesia is also a difficult problem for anesthesiologists who occasionally fail despite the fact that they attempt to over anesthetize the patient to ensure adequate anesthesia. Additional research is needed for developing a method in which adequacy may be estimated from the information obtained by the method of the present invention.

It is a yet further object of the present invention to add a capability to monitoring the anesthetic depth trends in real-time.

It is still further an object of the present invention to provide an apparatus to an anesthesiologist that during surgery would enable one to respond immediately to changes in anesthetic depth of the patient.

It is yet another object of the present invention to more accurately predict those changes in trend compared to monitoring of heart rate, blood pressure, etc. which are currently used.

The method of monitoring depth of anesthesia described here is expected to improve anesthesiologists capability to administer the correct amount of anesthesia. Using present methods, the anesthesiologist is always playing catch up to maintain the anesthetic level. The crude physiological variables that anesthesiologists are currently monitoring, such as heart rate and systolic blood pressure do not allow for immediate recognition of trends in the level of anesthesia. Because the described method monitors depth and trends in the anesthetic level in real-time, it enables more rapid control of the administered amounts of anesthetics.

The invention is a method and apparatus for collecting EEG data, transforming the EEG data, and correlating the transformed data with a depth of unconsciousness or anesthetic depth and obtaining a bounded first derivative for correlating trends of changes of anesthetic depth in real time.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 2b is smoothed data from FIG. 2a.

DESCRIPTION OF THE PREFERRED EMBODIMENT(S)

Figure 1:
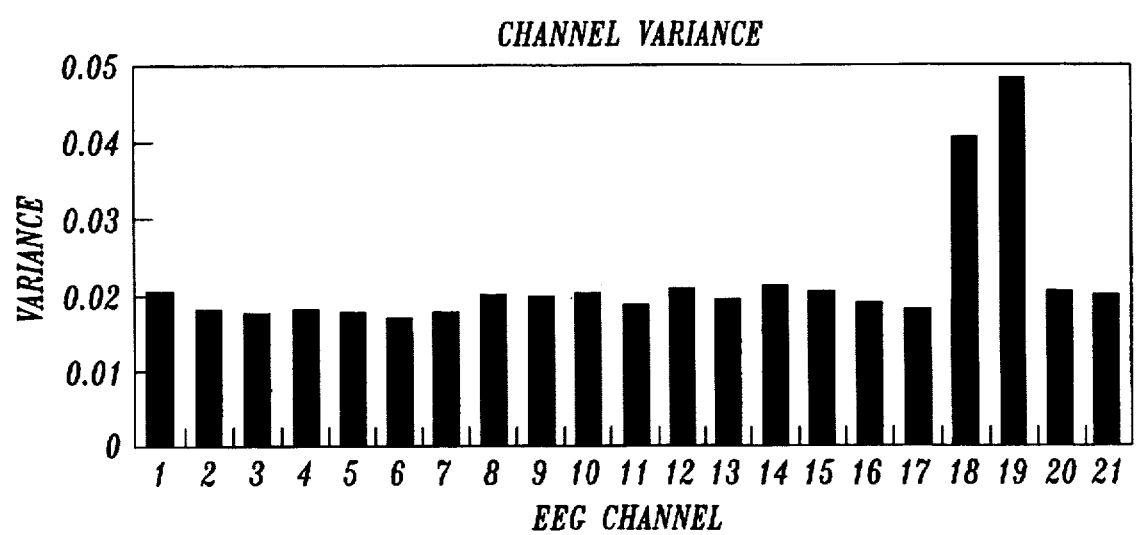
FIG. 1 is a bar chart showing channel variance of each EEG electrode.

According to the present invention, brain activity is monitored by an electroencephalogram (EEG). An electro-cap or headband containing a plurality of electrodes is used to collect the EEG data. The number of electrodes is at least 2, a reference, often attached to the ear, and one or more receiving electrodes placed on the head to collect EEG signals. Actual test information content across 21 different scalp electrodes with two reference electrodes attached to the ears for the purpose of determining depth of anesthesia showed that it may be possible to replace the cumbersome 21 electrode electro cap with a headband having possibly only three or four electrodes. The developed method may be combined with equipment such as Cadwell Laboratories' Spectrum 32 v4.3 signal analyzer in a medical device to aid an anesthesiologist in surgery. Because the device simplifies monitoring of anesthesia, it should also be considered for anesthetic administration by emergency medical personnel. These devices, including the developed method and the functionality of the Cadwell Laboratories' instrument, could be built into small portable devices that aid emergency medical personnel to administer anesthesia in the field during less than optimal conditions and with personnel who may not have the full training and experience of an anesthesiologist in a hospital environment.

Because it is generally believed that the auditory processing is a sense which disappears late during the induction of the anesthetic, one may therefore speculate that a patient is adequately anesthetized when the patient's auditory processing has disappeared. Accordingly, a preferred embodiment of the present invention further includes an external auditory signal to provoke a sensory perception in the patients which can be monitored. The hypothesis is that the patient's unconscious processing of this signal disappears when the patient is anesthetized to a depth when all auditory awareness has disappeared. An explicit response to the audio signal may or may not be found in any of the electrodes. To the extent that an explicit response is found while the patient is awake, that response may be monitored as an indication of depth of anesthesia thereby providing a "closed loop" system. The presence or absence of the explicit response is then an on-off indicator. If an explicit response to the audio signal is not identified when the patient is awake, then the operator may re-position the electrodes or seek other parameters.

In order to "teach" the artificial neural network (ANN), the EEG data must labelled initially. A number of samples of the EEG data were extracted a development set of patient data, when possible, from prior to induction, during induction, from approximately one hour after induction, during awakening, and from post awakening. These samples were labelled 0 if the patient was fully awake and 1 if deeply anesthetized. We labelled the data linearly from 0 to 1 over approximately four minutes during induction and from 1 to 0 during four minutes of awakening. We believe that lacking any other scientifically valid metric for depth of anesthesia, our approach is valid for our testing procedure because it is consistent across all patients.

The EEG signals are received by a signal processor wherein they are first windowed into consecutive samples, corresponding to a specific time interval according to the highest frequency to be sampled. The window should be long enough to obtain a good representation of frequency and short enough to rapidly recognize signal changes. The number of samples is not critical, but satisfactory results were obtained from 64 samples to 1024 samples. The longer window (greater number of samples) is preferred because it gives a better frequency resolution, reduces the effects of sporadic noise, while also being sufficient for detecting the slow changing events in the signal, i.e., the change in anesthetic depth.

Each window is transformed. The transformation may be a Laplace transform or Fourier transform into the frequency domain by using a Fourier transform obtaining real and imaginary coefficients. When a Fourier transform is used, either or both of the real and imaginary coefficients may be used to obtain magnitude coefficients. In a preferred embodiment, the Fourier transformed coefficients were further processed by computing magnitude coefficients from the real and imaginary coefficients. The frequency resolution was reduced by averaging every subgroup of magnitude coefficients into single bins. For 512 magnitude coefficients with 8 per subgroup resulted in a total of 64 bins of averaged spectral coefficients. These averaged spectral coefficients were adjusted by first subtracting an global average of the spectral coefficients, coefficient by coefficient. This subtraction removes the large amplitude variations that exist between different frequencies. Next, the adjusted averaged coefficients were normalized to one, excluding the smallest and largest 5% of the coefficient values. The exclusion of the extreme values is a common approach to remove outliers that are caused by noise. Normalizing within each spectrum removes the individual amplitude differences. The resulting spectrum allows for better comparison between the delta (0.5–3.5 Hz), theta (3.5–7.5 Hz), alpha (7.5–13.0 Hz), and beta (13.0–25.0 Hz) frequency bands which are known to be involved during thought processes.

The transformed data are input from the signal processor to a feedforward artificial neural network (ANN). A preferred configuration of the ANN is matching the number of input nodes to the number of coefficients from the transform. In a preferred embodiment, 64 input nodes were used to receive the averaged spectral coefficients, 5 hidden or internal processing nodes, and 1 processing/output node. The input nodes performed no processing of the averaged spectral coefficients. The hidden and output nodes used a sigmoidal activation function to analyze the non-linearities in the data. The development of an ANN consists of changing free variables (weights) in the ANN system to map the input vectors into output or target vectors. This approach used the backpropagation algorithm in an iterative process to change the free variables to cause the ANN system to correlate the spectral differences corresponding to different anesthetic depth labels. These free variables when adjusted become the capability to correctly predict the anesthetic depth and obtain a bounded first derivative from the EEG spectra acquired from a new patient in surgery.

The iterative process in which the ANNs are developed are completed according to specified criteria. Often this criterion is selected as a point when a mean square error (MSE) is minimized for a test data set which is periodically tested in parallel to the data set which is used for changing the free variables. The iterative processes in this development were continued while the MSE showed an obvious decrease. The MSE to be minimized was computed from the difference between each target anesthetic depth level and the level predicted by the ANN system.

A smoothed anesthetic depth prediction value at time t is computed as follows: smoothed value (t)=smoothed value (t−1)+(0.1* (actual anesthetic depth prediction (t)−smoothed value (t−of the predicted values received from the ANN system removes much of the sporadic variance caused by noise in the EEG signal. Other smoothing methods may be used. For example, the ANN configuration may change to a recurrent ANN in which the predicted depth is fed back into the ANN to restrict the amount this predicted value can change from time t to t+1.

One additional postprocessing step of these predicted values is done with a postprocessor. The step includes a bounded first derivative obtained by restricting the rate of change to physiological limits. The true or bounded maximum rate change of anesthetic depth of a patient may vary over several seconds, but is not expected to greatly change in less time. However, data collection and processing may occur in subsecond intervals that may include sporadic noise which show artificially large changes in predicted anesthetic depth. There are several ways to obtain a bounded first derivative. One way is to filter and smooth the anesthetic depth data so that all noise is eliminated. Another way is to average the instantaneous first derivative over a number of positions, for example ten positions to obtain a bounded first derivative. The bounded first derivative or slope is useful for ascertaining a trend of whether anesthetic depth is increasing or decreasing. Previous methods do not utilize a trend and therefore can undercorrect or overcorrect the amount of anesthesia administered to a patient.

EXAMPLE 1

The patient data for this research was collected by Dr. Harvey Edmonds during regularly scheduled carotid endarterectomy for carotid stenosis at Jewish Hospital and Norton Hospital. Both are research hospitals near the University of Louisville, Louisville, Ky.

The patients were anesthetized with inhalational agent isoflurane supplemented with intravenous agent midazolam. The patients were administered a continuous isoflurane vapor during surgery. The dosage of this vapor was adjusted to maintain depth of unconsciousness as assessed clinically from heart rate, blood pressure, etc.

The patients consented to the use of an electro cap containing electrodes to record 22 channel electroencephalography (EEG) data according to the international 10–20 EEG electrode placement system. The patients also wore a small earphone which generated a repetitive auditory signal at 40 Hz, (i.e., not a signal with a 40 Hz frequency but a signal which was turned on and off at a rate of 40 Hz (modulated at 40 Hz)).

Seven sets of data were collected from seven different individuals. The EEG data, consisting of a 22-channel monopolar montage, was continuously recorded during surgery with Cadwell Laboratories' Spectrum 32 v4.3 signal analyzer. The 22 channels of EEG data and one electrocardiogram channel were digitized at 200 Hz and 12 bit resolution.

Table 1 below shows the times that the recording of patient data was started and ended, the times that the patients were induced, and the times that the patients were observed to wake up. The table shows that there was no recording of data for Patient 1 prior to induction. There was also less than a minute available at the end of the recording when the patients were known to respond to the 40 Hz auditory signal and assumed to be waking up.

Table 1. The time interval for the data recording (start-end) and the time interval for anesthesia (induction-awake) for each patient.

| Patient | Start Time | Induction Time | Awake Time | End Time |
|---|---|---|---|---|
| 1 | 7:43 | 7:33 | 9:43 | 9:44 |
| 2 | 7:24 | 7:30 | 9:55 | 9:55 |
| 3 | 12:29 | 12:55 | 15:00 | 14:52 |
| 4 | 12:51 | 13:00 | 15:18 | 15:19 |
| 5 | 6:45 | 7:30 | 9:59 | 9:59 |
| 6 | 10:45 | 10:47 | 12:28 | 12:31 |
| 7 | 15:00 | 15:06 | 20:28 | 20:36 |

The times in Table 1 above were used as the basis for labelling 0 if the patient was fully awake and 1 if deeply anesthetized. We labelled the data linearly from 0 to 1 over approximately four minutes during induction and from 1 to 0 during four minutes of awakening.

The EEG signal in our approach is sampled at 200 Hz which according to the Nyquist law captures information in the 0–100 Hz range. Our EEG spectra will thus include the brains' repetitive sensory response to the modulated 40 Hz auditory signal.

The EEG signals were transformed into the frequency domain by using a Fourier transform. The continuous EEG was windowed into 1024 consecutive samples, corresponding to 5.12 seconds in time. Other window sizes as short as 64 samples also gave satisfactory results. The longer window was selected because it gives a better frequency resolution, reduces the effects of sporadic noise, while also being sufficient for detecting the slow changing events in the signal, i.e., the change in anesthetic depth.

The Fourier transformed coefficients were further processed by computing 512 magnitude coefficients from the real and imaginary coefficients. The frequency resolution was reduced by averaging every eight coefficients into a single bin for a total of 64 bins of averaged spectral coefficients. These spectra were adjusted by first subtracting an average spectrum, coefficient by coefficient. Next, each adjusted spectrum was normalized to one (1) after excluding the smallest and largest 5% of the coefficient values.

The preprocessed spectra were input to a feedforward artificial neural network (ANN). The configuration of the ANN used in the generation of the results below was 64 input nodes to receive the spectral coefficients, 5 hidden or internal processing nodes, and 1 processing/output node. The input nodes performed no processing of the spectral coefficients. The hidden and output nodes used a sigmoidal activation function to analyze the non-linearities in the data. This approach used the backpropagation algorithm in an iterative process to change the free variables to cause the ANN system to correlate the spectral differences corresponding to different anesthetic depth labels. These free variables when adjusted became the capability to correctly predict the anesthetic depth from the EEG spectra acquired from a new patient in surgery.

The iterative process in which the ANNs are developed were completed according to minimization of the mean square error (MSE). The iterative processes in this development were continued while the MSE showed an obvious decrease. The MSE to be minimized was computed from the difference between each target anesthetic depth level and the level predicted by the ANN system.

During both the data collection and development it was visually observed that the sensory response to the repetitive auditory signal at 40 Hz appeared at different locations on the scalp (EEG channels) for different patients. The question arose whether different locations should have been analyzed separately. The predictive capabilities of the different EEG channels are very uniform in this described approach as may be inferred from FIG. 1. This fact together with the relatively small number of patients available in this development precluded us from analyzing the EEG data for specific information at different locations.

FIG. 1 shows the variances in the predictive capabilities for each of the EEG channels averaged over approximately two hours of data from one patient. It shows that the individual EEG channels are about equally useful for predicting the depth of anesthesia. Only channels 18 and 19 show a significant difference in variance. The mean variance, not including channels 18 and 19, is 0.19164±0.00219 (0.19164±1.14%). Channels 18 and 19 are the Fz and Fpz electrode placements, respectively, according to the international 10–20 EEG electrode nomenclature.

The results showed that there is a significant predictive capability of the method of the present invention to determine depth of anesthesia. The method has a predictive capability because it can discriminate between the EEG spectra from the individual as awake and anesthetized. The results also show that the described method is capable of predicting the depth of anesthesia on a continuous scale between the extremes of fully awake and deeply anesthetized.

Our approach to make an unbiased evaluation of our method was to use a k-fold, also known as jack-knife or round robin, testing procedure. We used six of our seven valid patient data sets to develop our system and then tested the system with the seventh patient data set. We repeated this test seven times to test the system with all possible patient data sets without having used the testing data for a specific patient in the data used in developing each system.

Figure 2A:
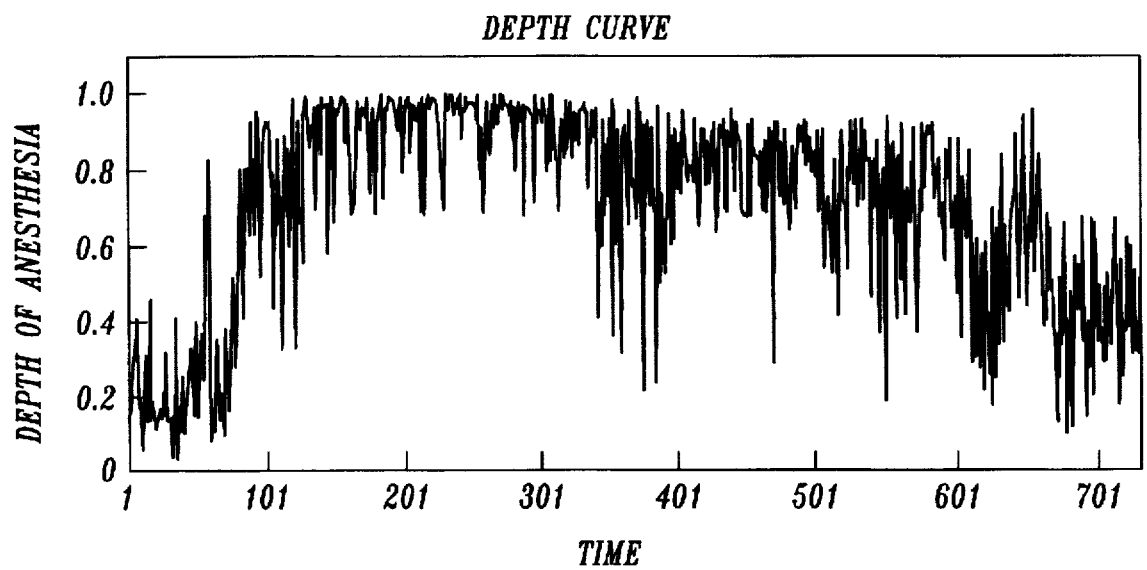
FIG. 2a is a graph of depth of anesthesia versus time from the ANN.
Figure 2B:
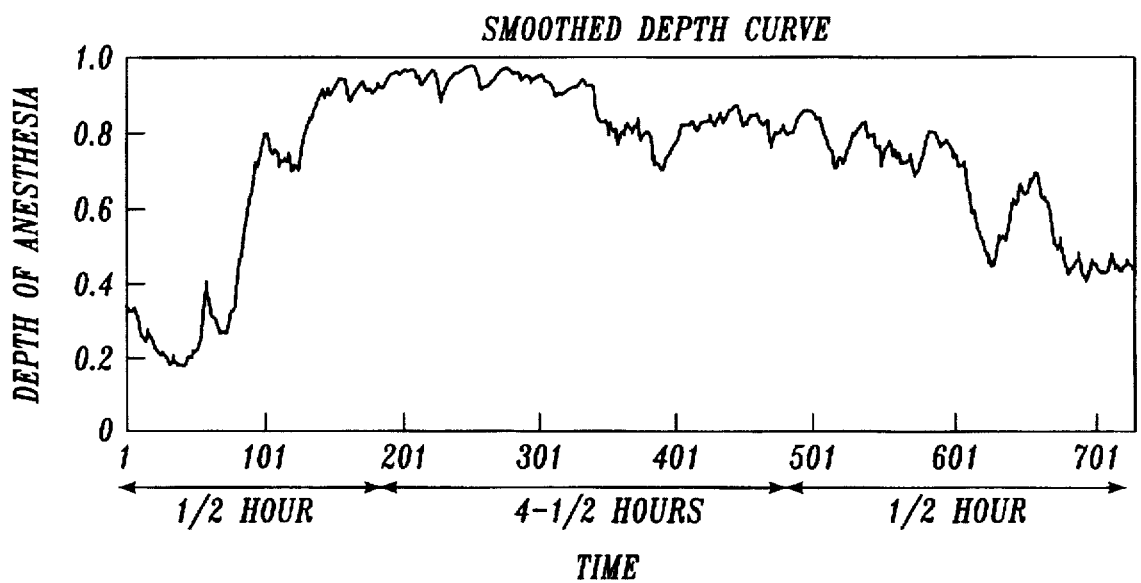

FIG. 2a and 2b show the anesthetic depth prediction from the EEG data of one patient. FIG. 2a shows the actual output from the ANN system, i.e., one anesthetic depth prediction value for each analyzed window of EEG waveform data. A window is a 5.12 second interval of EEG waveform or 1024 digitized samples. FIG. 2b shows a smoothed predicted anesthetic depth graph. FIGS. 2a and 2b show 730 predictions of depth of anesthesia during one five hour surgery procedure with approximately four and one half hours of data compressed during the middle of the surgery.

FIG. 2b shows a smoothed output. A smoothed anesthetic depth prediction value at time t is computed as follows: smoothed value (t)=smoothed value (t−)+(0.1* (actual anesthetic depth prediction (t)–smoothed value (t–))). The smoothing of the predicted values received from the ANN system removed much of the sporadic variance caused by noise in the EEG signal.

The graphed data in FIGS. 2a and 2b include the first 30 minutes and last 36 minutes of surgery intact and a sparse sampling of approximately four and one half hour of data from the steady state of anesthesia between the intact data. FIG. 2b shows that the patient is rapidly entering into anesthesia after induction at approximately window 70 on the horizontal axes. The patient is in a fully anesthetized state from approximately window 150 until the continuous administering of anesthetic was ceased at approximately window 580. This patient started to respond to external stimuli at the end of the graph (surgery) when the anesthetic depth level fell below 0.5. Note that although the scale for the anesthetic depth ranging from 0 to 1 may be translated into awake, indeterminate, and adequately anesthetized, it is not based on a true metric.

Table 2 shows the number of spectra used from each patient and the capability to predict depth of anesthesia. The low and high numbers of spectra are the number of spectra that were labelled as anesthetic level below 0.5 and above 0.5, respectively. The low and high mean values are the means of the predicted depth of anesthesia for the two sets of spectra for each patient.

TABLE 2

Number of spectra used from each patient

| Patient | Low Spectra | High Spectra | Total Spectra | Low Mean | High Mean | Training MSE | Test MSE |
|---------|-------------|--------------|---------------|----------|-----------|--------------|----------|
| 1 | 2354 | 2354 | 4708 | 0.5538 | 0.5685 | 0.078 | 0.2958 |
| 2 | 1276 | 1870 | 3146 | 0.4603 | 0.6586 | 0.079 | 0.0124 |
| 3 | 638 | 1782 | 2420 | 0.4989 | 0.5894 | 0.081 | 0.147 |
| 4 | 880 | 2420 | 3300 | 0.36 | 0.6222 | 0.077 | 0.146 |
| 5 | 1760 | 1340 | 3100 | 0.502 | 0.8396 | 0.082 | 0.151 |
| 6 | 814 | 1012 | 1826 | 0.5723 | 0.7647 | 0.078 | 0.141 |
| 7 | 2904 | 2420 | 5324 | 0.4061 | 0.7093 | 0.073 | 0.137 |
| Total: | 10626 | 13198 | 23824 | | Mean: | 0.0913 | 0.1717 |

Table 3 below shows that the method of the present invention has a statistically significant capability to predict the state of an individual—awake or anesthetized. This table shows the significance of the means presented in Table 2. The Mann-Whitney U—Wilcoxon Rank Sum W test shows that the low and high means for each patient are significantly different, i.e., there is 100% confidence that the samples come from populations with different means. The small difference in the means and the large MSE for Patient 1 in Table 2 appear to suggest poor predictive results. Table 3 does show that there is still significant predictive capability demonstrated in the test with Patient 1.

TABLE 3

Mann-Whitney U - Wilcoxon Rank Sum W Test Data

| Patient | IZI | Exact 1-tailed P | Corrected for ties 1-tailed P |
|---------|-----|------------------|-------------------------------|
| 1 | 20.958 | 0.0103 | 0.0000 |
| 2 | 118.7052 | 0.0000 | 0.0000 |
| 3 | 23.8475 | 0.0000 | 0.0000 |
| 4 | 103.9112 | 0.0000 | 0.0000 |
| 5 | 297.1358 | 0.0000 | 0.0000 |

TABLE 3-continued

Mann-Whitney U - Wilcoxon Rank Sum W Test Data

| Patient | IZI | Exact 1-tailed P | Corrected for ties 1-tailed P |
|---------|-----|------------------|-------------------------------|
| 6 | 36.7396 | 0.0000 | 0.0000 |
| 7 | 679.8995 | 0.0000 | 0.0000 |

Figure 3:
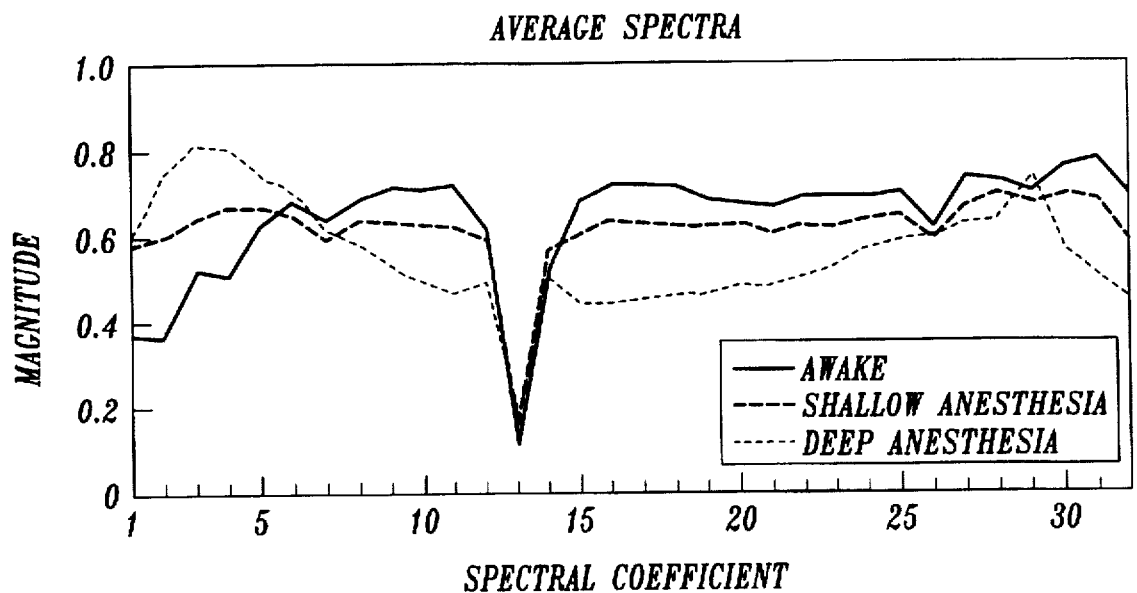
FIG. 3 is average spectra data including a notch at 40 Hz.

In FIG. 3 the spectra range from 0–100 Hz on the horizontal axis. The graph shows a large drop in magnitude at spectral coefficient 13, corresponding to about 40 Hz. This is an artifact in the form of a notch filter caused by the signal processing and normalization which removes a constant frequency such as the 40 Hz signal that is put into system.

Figure 4:
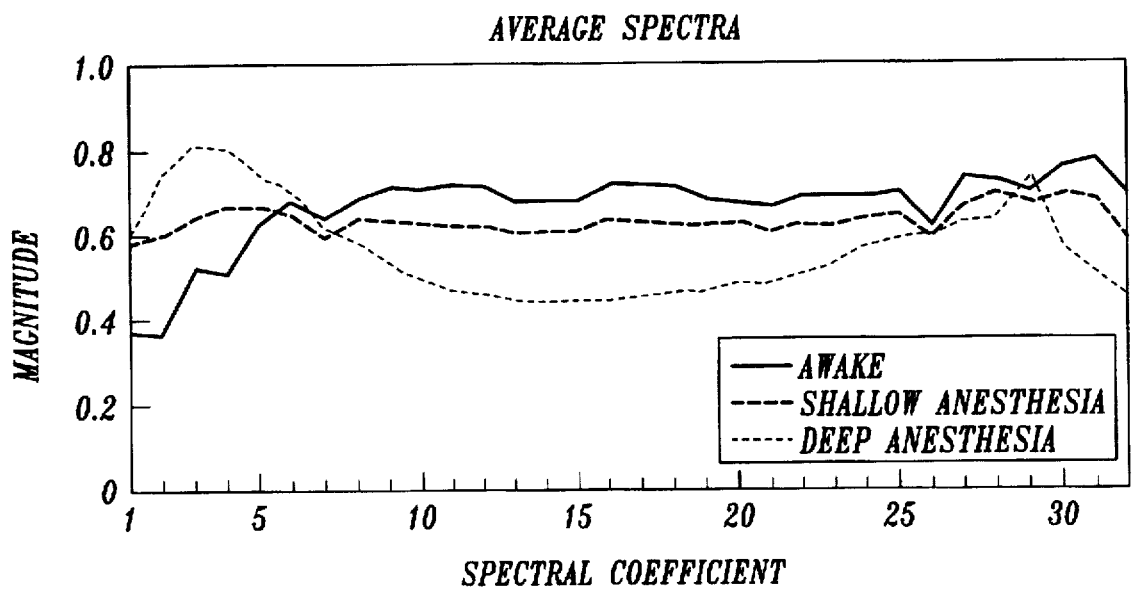
FIG. 4 is average spectra data with the notch removed.

FIG. 4 shows that there are significant differences between the EEG spectra of patients being awake and anesthetized. The shallow anesthesia graph shows that there is a continuous change in the spectra between the extremes of awake and deep anesthesia. The ANN system was developed to use these differences to predict depth of anesthesia and to recognize trends indicating that a patient's anesthetic state is becoming shallower or deeper as shown in FIG. 2. The graph (FIG. 4) shows the average spectra from FIG. 3 but with the 40 Hz notch manually removed to bring clarity to the information content of the graph. The graph shows a significant difference between the average EEG spectra for the seven patients awake and in deep anesthesia. The graph also shows that the average spectra of shallow anesthesia is between the other two spectra. One expects to see a continuum of spectra between the two extreme spectra depending on the depth of the anesthesia.

Figure 6:
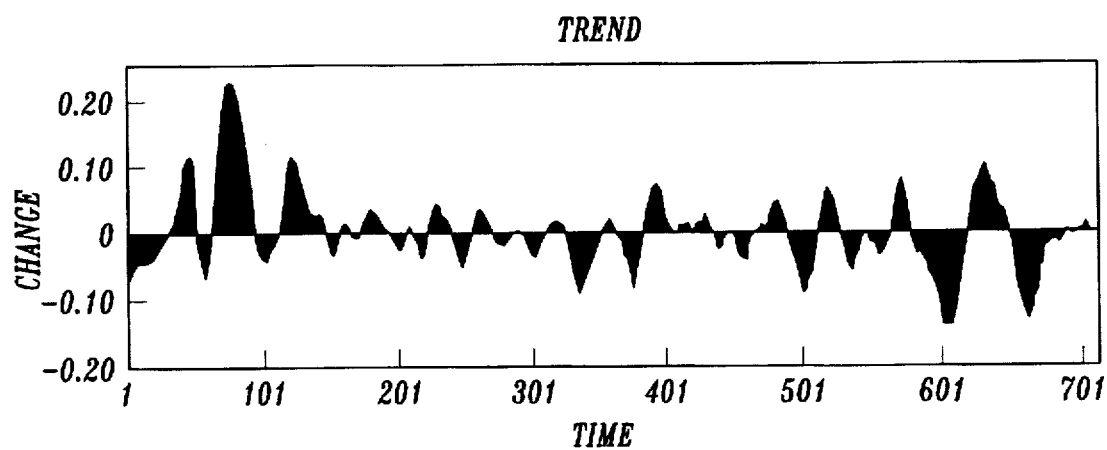
FIG. 6 is a graph of bounded first derivatives of the smoothed data from FIG. 2b.

A bounded first derivative is shown in FIG. 6 corresponding to the smoothed depth curve of FIG. 2b. Positive values of the "change" or bounded first derivative indicate an increase in anesthetic depth and negative values indicate a decrease in anesthetic depth. Ideally, a patient should be held constant during surgery. In this example, it is apparent that use of standard methods permitted variation in anesthetic depth during surgery. The bounded first derivatives of FIG. 6 were obtained by averaging ten points behind time (t), averaging ten points ahead of time (t), then computing the slope between the averaged points.

EXAMPLE 2

Figure 5:
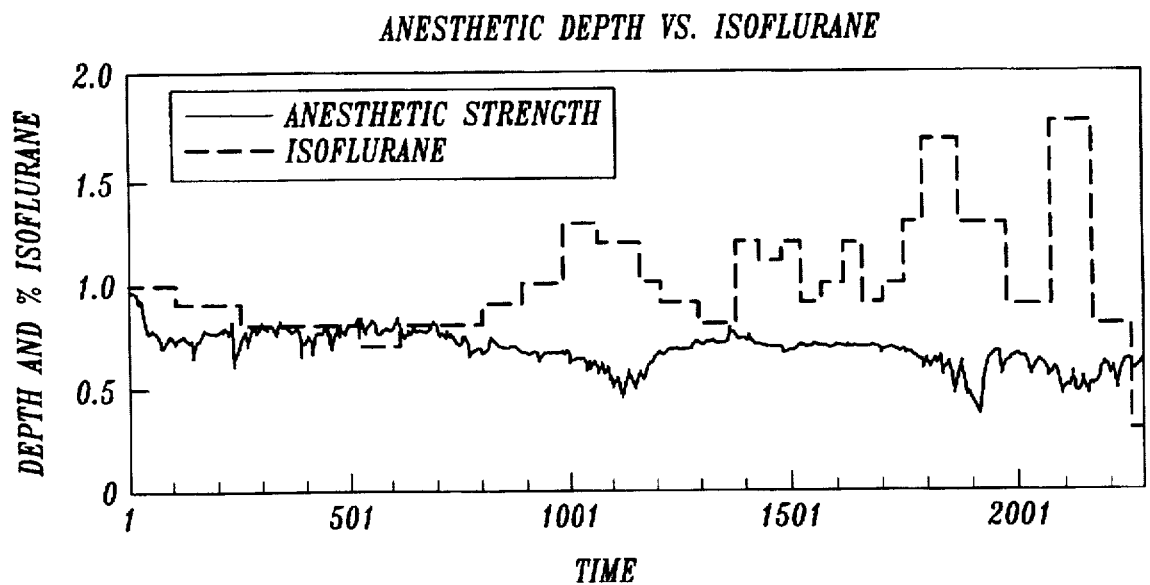
FIG. 5 is a graph showing anesthetic depth together with isoflurane (anesthetic) concentration.

Breath analysis was combined with the EEG data in FIG. 5 showing that there is a significant correlation between the exhaled concentration of isoflurane and the depth of anesthesia. The correlation coefficient is (–)0.5616 over a four hour period in the patient depicted in FIG. 5. The exhaled concentration of isoflurane is directly proportional to the arterial concentration of isoflurane and thus also the concentration arriving shortly to the brain where the anesthetic depth is measured by EEG. The anesthesiologist increases and decreases the isoflurane vapor to maintain the patient's anesthetic level by monitoring systolic blood pressure, heart rate, etc. For example, FIG. 5 shows that the patient's anesthetic depth is becoming shallower at approximate 700 on the horizontal axis. The anesthesiologist counteracts this by increasing the isoflurane vapor to the patient. The patient's response, including a time lag, is visible at 1150 where the patient's anesthetic depth is increasing.

The FIG. 5 shows the relationship between the isoflurane end tidal concentration and the depth of anesthesia. The horizontal axis covers approximately 4 hrs of surgery in one patient. The anesthetic depth ranges from 0 to 1, 0 being fully awake and 1 fully anesthetized. The graph shows that the anesthetic depth and the exhaled concentration of isoflurane is negatively correlated. These phenomena are most clear at approximately 1000, 1800, and 2100 on the horizontal axis.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of monitoring an anesthetic depth of a person, comprising the steps of:
   (a) placing a plurality of EEG electrodes on the person's head;
   (b) obtaining an EEG signal continuously from each of said EEG electrodes;
   (c) windowing said continuous EEG signal into consecutive samples;
   (d) transforming from a time domain to a frequency domain each of said consecutive samples of the EEG signal; and
   (e) inputting said transformed consecutive samples into an artificial neural network having a plurality of input nodes and one output node, and correlating said transformed consecutive samples with said anesthetic depth as a scaled numeric value.

2. The method as recited in claim 1, further comprising the step of:
   (f) obtaining a bounded first derivative of said correlation for obtaining a trend.

3. The method as recited in claim 2, wherein said bounded first derivative is obtained from a slope between points averaged ahead of and behind a time (t).

4. The method as recited in claim 2, wherein said anesthetic depth and said trend are updated continuously.

5. The method as recited in claim 4, wherein updated continuously is at least every second.

6. The method as recited in claim 1, wherein said transforming is with a Fourier transform obtaining real and imaginary coefficients.

7. The method as recited in claim 6, further comprising obtaining magnitude coefficients from said Fourier transform, and binning said magnitude coefficients.

8. The method as recited in claim 7, further comprising the step of adjusting the binned magnitude coefficients.

9. The method as recited in claim 8, wherein adjusting comprises the steps of:
   (a) subtracting an average spectrum, coefficient by coefficient and obtaining coefficient differences.

10. The method as recited in claim 7, wherein inputting comprises the steps of:
    (a) entering a binned magnitude coefficient into a particular input node of the artificial neural network.

11. The method as recited in claim 1, wherein said windowing contains at least 64 samples.

12. The method as recited in claim 1, wherein inputting comprises the steps of:
    (a) entering a single magnitude coefficient into a particular input node of the artificial neural network.

13. An apparatus for monitoring an anesthetic depth of a person, comprising:
    (a) a plurality of EEG electrodes on the person's head;
    (b) a signal processor that receives a spectra of EEG signal from each of said EEG electrodes, and transforms said spectra of EEG signal from a time domain to a frequency domain into magnitude coefficients; and
    (c) an artificial neural network having a plurality of input nodes and one output node, said plurality of input nodes that receives said magnitude coefficients from said signal processor and correlates said magnitude coefficients with said anesthetic depth as a scaled numeric value.

14. The apparatus as recited in claim 13, further comprising:
    (d) a post processor that obtains a bounded first derivative of said anesthetic depth.

15. A method of monitoring an anesthetic depth of a person, comprising the steps of:
    (a) placing a plurality of EEG electrodes on the person's head;
    (b) obtaining an EEG signal continuously from each of said EEG electrodes;
    (c) windowing said continuous EEG signal into consecutive samples;
    (d) transforming each of said consecutive samples of the EEG signal;
    (e) inputting said transformed consecutive samples into an artificial neural network and correlating said transformed signal with said anesthetic depth; and
    (f) obtaining a bounded first derivative of said correlation for obtaining a trend.

16. The method as recited in claim 15, wherein said transforming is with a Fourier transform obtaining real and imaginary coefficients.

17. The method as recited in claim 16, further comprising obtaining magnitude coefficients from said Fourier transform, and binning said magnitude coefficients.

18. The method as recited in claim 15, wherein said windowing contains at least 64 samples.

19. The method as recited in claim 15, wherein said bounded first derivative is obtained from a slope between points averaged ahead of and behind a time (t).

20. The method as recited in claim 15, wherein said anesthetic depth and said trend are updated continuously.

* * * * *

UNITED STATES PATENT AND TRADEMARK OFFICE
CERTIFICATE OF CORRECTION

PATENT NO. : 5,775,330
DATED : 07/07/98
INVENTOR(S) : Lars J. Kangas, Paul E. Keller It is certified that error appears in the above-identified patent and that said Letters Patent is hereby corrected as shown below:

In column 6, line 22, please change "value (t-of the" to --value (t-1))). The smoothing of the--.

Signed and Sealed this

Twenty-sixth Day of January, 1999

Attest:

Attesting Officer

*Acting Commissioner of Patents and Trademarks*